United States Patent [19]

Gray et al.

[11] Patent Number: 5,686,422
[45] Date of Patent: Nov. 11, 1997

[54] SYNTHETIC INHIBITORS OF MAMMALIAN COLLAGENASE

[75] Inventors: Robert D. Gray; Arno F. Spatola, both of Louisville, Ky.; Robert B. Miller, Vernon Hills, Ill.; Frank R. Burns; Christopher Paterson, both of Louisville, Ky.

[73] Assignee: Research Corporation Technologies, Inc., Tucson, Ariz.

[21] Appl. No.: 468,491

[22] Filed: Jun. 6, 1995

Related U.S. Application Data

[63] Continuation of Ser. No. 207,005, Mar. 7, 1994, abandoned, which is a continuation of Ser. No. 807,775, Dec. 9, 1991, abandoned, which is a continuation of Ser. No. 312,531, Feb. 17, 1989, abandoned, which is a continuation-in-part of Ser. No. 26,933, Mar. 17, 1987, abandoned.

[51] Int. Cl.$^6$ .................................................. A61K 37/00
[52] U.S. Cl. .................................................. 514/18
[58] Field of Search .................................................. 514/18

[56] References Cited

U.S. PATENT DOCUMENTS

| | | | |
|---|---|---|---|
| 4,113,715 | 9/1978 | Ondetti et al. | 548/523 |
| 4,146,611 | 3/1979 | Ondetti et al. | 514/19 |
| 4,154,946 | 5/1979 | Ondetti et al. | 548/312.7 |
| 4,263,293 | 4/1981 | Sundeen et al. | 424/248.5 |
| 4,297,275 | 10/1981 | Sundeen et al. | 530/332 |
| 4,327,111 | 4/1982 | Sundeen et al. | 424/278 |
| 4,361,574 | 11/1982 | Grant et al. | 424/270 |
| 4,367,233 | 1/1983 | Clark et al. | 424/470 |
| 4,371,465 | 2/1983 | McGregor | 530/330 |
| 4,371,466 | 2/1983 | McGregor | 530/329 |
| 4,374,765 | 2/1983 | McGregor | 514/19 |
| 4,382,081 | 5/1983 | Sundeen et al. | 424/278 |
| 4,474,799 | 10/1984 | Greenberg et al. | 514/415 |
| 4,500,467 | 2/1985 | Kubinyi et al. | 514/19 |
| 4,511,504 | 4/1985 | McCullagh et al. | 424/177 |
| 4,560,506 | 12/1985 | Weller, III et al. | |
| 4,595,700 | 6/1986 | Donald et al. | 514/616 |
| 4,599,361 | 7/1986 | Dickens et al. | 514/575 |
| 4,611,002 | 9/1986 | Ondetti | 514/419 |
| 4,613,587 | 9/1986 | Kessler et al. | 514/19 |
| 4,681,966 | 7/1987 | Donald et al. | 558/255 |
| 4,687,841 | 8/1987 | Spilburg et al. | 530/331 |
| 4,743,587 | 5/1988 | Dickens et al. | 514/575 |

FOREIGN PATENT DOCUMENTS

| | | |
|---|---|---|
| 0 149 593 | 7/1985 | European Pat. Off. |
| 0 214 639 | 3/1987 | European Pat. Off. |
| 0 236 872 | 9/1987 | European Pat. Off. |

OTHER PUBLICATIONS

Chem. Abstracts 100 (1984) 2646x.
Matsueda, *Chemistry Letters*, Oct. 3, 1985, No. 7, pp. 1041–1044.
Delaisse, *Biochemical & Biophys. Research Comm.*, 1985, 133, 483–490.
Gray et al. *Fed. Proc.*, 44, 1432 (1985).
Gray et al., *The Journal of Biochemistry*, 1986, 32:71–77.
Gross et al. *The Peptides*, vol. 1, 45–48 (1979).
Kessler et al., *Infect. Immun.* (1983) 38(2), 716–23.
Liotta, *AJP*, 117, 339–348 (1984).
Gray et al., *Faseb J.*, 1988, 2, A345.
Miller et al., *Federal Proceedings*, 1986, 45:1859.
Mooktiar et al., *Biochemistry*, 1987, 26, 1962–1965.
Reich, *Cancer Research*, 48, 3307–3312 (1988).
Rudinger, *Peptide Hormones*, 1976, pp. 1–7, "Characteristics of the amino acids as components of a peptide hormone sequence".
The Merck Manual of Diagnosis and Therapy, 11th Ed. 948–55 and 374–381.
The Merck Manual, 11th Ed. (1966), 988–989.
Gray, et al., *Biochemical and Biophysical Research Communications*, 1981, 101, 1251–1258.
Blumberg et al., *Eur. J. Biochem.* 1983 136(1), 151–4.
Chem. Abstracts, 104, 17982n (1986).
Chem. Abstracts, 84, 117624g (1976).
Chem. Abstracts, 98 27344a (1983).

*Primary Examiner*—Edward J. Cain
*Attorney, Agent, or Firm*—Scully, Scott, Murphy and Presser

[57] ABSTRACT

The present invention relates to compounds of the formula:

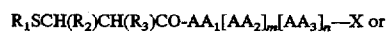

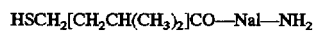

wherein Nal is L-3-(2-naphthyl)alanine;

m is the integer 0 or 1; n is an integer from 0–2;

$AA_1$ is a non-polar hydrophobic aromatic amino acid;

$AA_2$ is alanine, glycine, leucine, isoleucine or phenylalanine;

$AA_3$ is one of the twenty naturally occurring amino acids, preferably glutamine or arginine;

$R_1$ is hydrogen, alkyl having from 1–10 carbon atoms, alkanoyl having from 2–10 carbon atoms, or aroyl having from 7–10 carbon atoms;

$R_2$ is hydrogen or alkyl having from 1–6 carbon atoms;

$R_3$ is hydrogen, alkyl having from 2–10 carbon atoms, cycloalkyl having from 3–6 carbon atoms, aryl or arylalkyl, wherein aryl moieties have from 6–10 carbon atoms;

X is $NH_2$, OH, $OCH_3$ or $OCH_2CH_3$;

and salts thereof.

96 Claims, No Drawings

SYNTHETIC INHIBITORS OF MAMMALIAN COLLAGENASE

REFERENCE TO THE RELATED APPLICATION

This is a File Wrapper Continuation of Ser. No. 207,005, filed Mar. 7, 1994 now abandoned which is a continuation of Ser. No. 807,775 filed on Dec. 9, 1991, which is a File Wrapper Continuation of U.S. Ser. No. 312,531 filed Feb. 17, 1989, now abandoned, which is a continuation-in-part of application Ser. No. 026,933 filed on Mar. 17, 1987, now abandoned.

GOVERNMENT SPONSORSHIP

This work has been supported by a grant from the National Institute of Health, Grant Nos. AM 31364, EY 06918, AR 39573 and F32-EY06048-01A1.

BACKGROUND OF THE DISCLOSURE

1. Field of the Invention

The present invention relates to novel synthetic peptides. More particularly, the invention relates to novel peptides which are useful as inhibitors of mammalian collagenase.

2. Background of the Prior Art

Collagenases are proteolytic enzymes which initiate the degradation of collagen in vertebrates. In addition to their normal function in metabolism of connective tissue and wound healing, these endoproteinases have been implicated in a number of pathological conditions such as joint destruction in rheumatoid arthritis, periodontal disease, corneal ulceration and tumor metastasis.

Of particular significance is the pathological condition caused by corneal ulceration. Corneal ulceration is caused by different agents. One such cause is alkali burning of the cornea. Although methods of treatment are known, treatment of this condition continues to be a major challenge in ophthalmology.

Many therapeutic techniques have been used in an attempt to prevent the sequellae which threaten the integrity of the eye following a chemical injury. These include corticosteroids, heparin, collagenase inhibitors, contact lenses, fibronectin, conjunctival flaps, and corneal transplantation. Recent studies have advocated the use of sodium citrate and sodium ascorbate. Following an ocular alkali burn, a number of degradative processes occur which may result in a corneal ulcer. Several proteases, including collagenase, are elaborated in the chemically injured cornea and account for the ulcerative process. Although the multitude of treatment modalities used in these injuries undoubtedly work by different mechanisms of action, successful management of ocular alkali burns requires the use of agents which reduce the impact of collagenase and other proteases upon the cornea.

The efficacy of inhibitors of collagenase for use in human corneal alkali burns is open to question. Compounds which have been tested experimentally in animals include acetylcysteine, cysteine, sodium and calcium EDTA, and penicillamine. Of these, acetylcysteine which is approved for use as a mucolytic agent, is the only collagenase inhibitor used clinically in the treatment of human alkali burns. Its efficacy has yet to be proven in a randomized clinical trial. Collagenase inhibition by the tetracycline family of antibiotics has been demonstrated in vitro and systemic tetracycline has recently been shown to inhibit alkali-induced corneal ulceration in rabbits. Thus, an adequate inhibitor of collagenase for the treatment of alkali-induced corneal ulceration has not yet been developed and is a desired goal in ophthalmology.

Another cause of corneal ulceration is infectious keratitis. Infectious keratitis is the most common and most serious of the ocular infections. The organism *Pseudomonas aeruginosa* (PA) is one of the leading causes of infectious keratitis. The mainstay of therapy for infectious keratitis has been antimicrobial agents, but often, even when adequate levels of antibiotics are delivered, keratitis can progress to corneal ulceration and perforation. Many organisms, such as PA, release destructive enzymes which contribute to the breakdown of the cornea. In addition to enzymes released by the organism, host-derived enzymes, such as corneal collagenase, are also involved in the pathogenesis of infectious keratitis. Again, a new treatment for this condition is clearly a major current need in opthalmology.

Another area where collagenase inhibitors may be clinically important is the control of tumor metastasis. Malignant tumor cells differ from other cancer cells in their ability to spread through the mammalian body. To do this these cells must destroy connective tissue by giving off proteolylic enzymes including collagenases. It is thus postulated that collagenase inhibitors may slow down or even stop metastasis by inhibiting these enzymes.

The mechanism of action of mammalian collagenases on the molecular level is fairly well understood. Tissue collagenases hydrolyze a specific peptide bond at a single cleavage site on each of the three collagen chains of triple helical collagen. This cleavage site is contained within the amino acid sequence Pro-Gln-Gly-Leu-(Ile-)-Ala-Gly-Gln-Arg, with cleavage occurring between glycine 775 and leucine or isoleucine 776, in Types I, II and III collagen, the predominant collagen in skin, bone, tendon, dentin, fascia and cartilage. Type IV collagenase (gelatinase) degrades basement membrane (Type IV) collagen, which may be important in tumor metastasis. The collagenases are metallopeptidases which contain an essential zinc at the active site. The zinc is assumed to function by interactions with the scissile carbonyl of the substrate, thus facilitating hydrolysis of the peptide bond.

Compounds which coordinate to the zinc active site have the ability to inhibit the activity of the collagenase. Because of the clinical importance and the desirability of being able to control these enzymes' activity, there has been a widespread effort to design compounds which are capable of interacting with the enzyme binding site and preventing the enzymes' action. Consequently, there exists a number of synthetic peptides and chemically similar compounds which are claimed to have at least some effect in inhibiting the activity of mammalian collagenases. Many of these synthetic peptides are constructed so as to mimic the natural amino acid sequence flanking the collagenase cleavage site. For example, U.S. Pat. No. 4,511,504 describes a number of carboxyalkyl peptide derivatives said to have inhibitory activity. U.S. Pat. No. 4,263,293 relates to heterocyclic-containing amide compounds, U.S. Pat. No. 4,235,885 discloses mercaptoacyl amino acid derivatives, U.S. Pat. No. 4,327,111 teaches N-substituted mercaptoacyl propionamides, U.S. Pat. No. 4,382,081 describes a wide variety of mercapto amino acid derivatives, all of which appear to have some level of collagenase inhibitory activity. Similarly, U.S. Pat. No. 4,374,765 refers to the use of acyl derivatives of the peptide Gly-L-Cys-Gly-L-Gln-L-Glu-NH$_2$. U.S. Pat. No. 4,367,233 refers to thioglycolic acid derivatives, and U.S. Pat. No. 4,361,574 teaches alkanoic acid derivatives which are useful collagenase inhibitors. U.S. Pat. No. 4,687,841 describes peptide hydroxamic acids.

U.S. Pat. No. 4,595,700 sets forth thiol-based inhibitors. U.S. Pat. No. 4,599,361 teaches hydroxamic acid collagenase inhibitors. European Patent Application No. 85870005.7 discloses thiopeptolide derivatives as inhibiting collagenase substrates. European Patent Application Nos. 87102771.0 and 86112386.7 discloses hydroxamic based collagenase inhibitors.

In addition to patents, the scientific literature also contains references to many collagenase inhibiting compounds. Clark, et al. (*Life Sciences* 37: 575–578 (1985) refer to N[[5-chloro-2-benzo thiazolyl)thiophenyl]acetyl]-L-cysteine, said to be a powerful mammalian collagenase inhibitor. Deleaisse, et al. (*Biochem Biophys. Res. Comm.* 133: 483–490, 1985) also refer to an inhibitor N-[3-N-(benzyloxy-carbonyl)amino-1-(R)-carboxypropyl]-L-leucyl-O-methyl-L-tyrosine-N-methylamide. Gray, et al. (*Biochem. Biophys. Res. Comm.* 101: 1251–1258, 1981) disclose a number of thio-containing analogues of the collagen cleavage site. Additional thiol-containing peptides are disclosed by Gray, et al. in *J. Cell Biochem.*, 32: 71–77, 1986. Carboxyalkyl peptide analogues are described by Gray, et al. in *Federation Proc.* 44: 1431, 1985. Miller, et al. and Gray et al. also disclose thiol-containing peptides in abstracts. [*Fed. Proc.* 45:1859 (1986) and *SASEB J.* 2: A345 (1988), respectively]. Mookhtiar et al. also discloses phosphonamidate inhibitors of collagenase. (*Biochemistry*, 26, 1962 (1987)).

Despite the large number of compounds showing inhibitory properties, the therapeutically useful commercially available compounds are very few in number and are not altogether satisfactory in all respects for clinical use. Therefore, a continued need exists for an extremely potent and highly specific collagenase inhibitor which will have widespread therapeutic and commercial application. It has now been discovered that a small class of novel thiol-containing peptides provides a level of collagenase inhibition not heretofore observed in the known inhibitory compound.

BRIEF DESCRIPTION OF THE INVENTION

The present invention relates to peptides of the formulae:

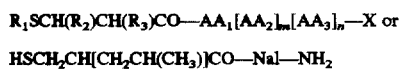

$HSCH_2CH[CH_2CH(CH_3)]CO—Nal—NH_2$ wherein Nal is the amino acid, naphthylalanine; m is the integer of 0 or 1; n is an integer from 0–2;

$AA_1$ is a non-polar hydrophobic aromatic amino acid or ε-amino blocked lysine;

$AA_2$ is an amino acid selected from the group consisting of alanine, glycine, leucine, isoleucine and phenylalanine;

$AA_3$ is an amino acid selected from the group consisting of the twenty naturally occurring amino acids;

$R_1$ is hydrogen, alkyl having from 1–10 carbon atoms, alkanoyl having from 2–10 carbon atoms, or aroyl having from 7–11 carbon atoms;

$R_2$ is hydrogen or alkyl having from 1–6 carbon atoms;

$R_3$ is hydrogen or alkyl having from 2–10 carbon atoms, cycloalkyl having from 3–6 carbon atoms, aryl or arylalkyl, wherein the aryl moiety has from 6–10 carbon atoms;

X is $NH_2$, OH, $—OCH_3$ or $—OCH_2CH_3$, and salts thereof.

The present invention also encompasses pharmaceutical compositions containing the aforementioned peptides as well as a method of treatment of collagenase-related disorders which comprises administration of an inhibitory effective amount of one or more of the claimed peptides.

The twenty naturally occurring amino acids are recited below with the abbreviation for each used hereinafter in the specification and claims:

| | |
|---|---|
| Ala - Alanine | Thr - Threonine |
| Gly - Glycine | Cys - Cysteine |
| His - Histidine | Met - Methionine |
| Leu - Leucine | Pro - Proline |
| Ile - Isoleucine | Lys - Lysine |
| Ser - Serine | Arg - Arginine |
| Asp - Aspartic Acid | Asn - Asparagine |
| Glu - Glutamic Acid | Gln - Glutamine and |
| Phe - Phenylalanine | Tyr - Tyrosine |
| Trp - Tryptophan | Val - Valine |

In addition, as used in the specification, the abbreviation for L-3-(2-naphthyl)alanine is Nal.

DETAILED DESCRIPTION OF THE INVENTION

The peptides of the present invention represent inhibitory, thiol-containing analogues of the carboxyl side of the natural cleavage site of the collagen molecule. These novel peptides exhibit a very high affinity for this binding site of collagenase. The specificity and inhibitory activity of these compounds is greater than that observed with any commercially available collagenase inhibitors. A particularly surprising feature of the present peptides is the fact that the amino acid adjacent to the metal coordinating functionality, i.e. the thiol group, should preferably be a hydrophobic amino acid. This is a departure from the arrangement of the natural cleavage site in which alanine, an aliphatic neutral amino acid, occupies the corresponding position relative to the scissile carbonyl. Previously described synthetic peptide analogues have therefore tended to be constructed along the same lines, i.e., using a neutral amino acid such as leucine, isoleucine, alanine or glycine adjacent to the metal binding functionalities. It thus is particularly unexpected that not only does the use of a hydrophobic amino acid provide an active inhibitor, but is also provides a superior inhibitor.

The peptides of the present invention preferably may contain one, and up to four, amino acid residues. Additionally amino acid residues may be present but do not add substantially to the activity of the product and simply serve to complicate the preparation of the peptide. The peptide structure is combined with a thiol-containing functional moiety which serves to bind to the zinc at the active site with the collagenase enzyme. The thiol-containing moiety in the final peptide has the formula:

wherein $R_1$ is hydrogen, alkyl, alkanoyl, or aroyl; $R_2$ is hydrogen or alkyl, and $R_3$ is hydrogen, alkyl cycloalkyl, aryl or aralkyl. The alkanoyl moieties in the foregoing formula contain from 2–10 carbon atoms; the preferred alkanoyl moiety is acetyl. The aroyl substituents contain from 7–11 carbon atoms, with benzoyl being particularly preferred. Alkyl moieties contain from 2–10, and preferably from 2–6, carbon atoms and may be straight-chain or branched; isobutyl is the particularly preferred alkyl substituent. Aryl and the aryl in arylalkyl contain from 6–10 carbon atoms; the preferred aryl is phenyl. It will also be understood that the aryl moieties may be substituted with one, two or three substituents selected from the following alkyl, alkoxy, amino, hydroxy, or alkanyloxy, the alkylalkoxy and alkanoyloxy moieties containing from 1–6 carbon atoms. Overall, the preferred thiol-containing moiety is one in which $R_1$ is hydrogen, $R_2$ is hydrogen or methyl and $R_3$ is alkyl, preferably isobutyl.

As noted above, one of the most essential elements of the peptide is the presence of a non-polar hydrophobic amino acid at the position one amino acid removed from the carbonyl functionality. As used herein, the term non-polar hydrophobic amino acid is a non-polar aromatic or heteroaromatic amino acid or an ε-amino-blocked lysine. This amino acid may be selected from among the naturally occurring amino acids such as phenylalanine, tryptophan, tyrosine, or ε-amino blocked lysine, or may be a synthetic aromatic amino acid such as naphthylalanine. It is possible to construct a highly effective inhibitor with the presence of a single amino acid of this type, for example, the compound 1 and 2 of Table I.

The presence of a second amino acid is usually preferred and can increase the activity of the inhibitors substantially. The choice of residue at this position is also narrowly limited, however, if activity is to be maximized. The amino acid at this position is preferably selected from the group consisting of alanine, glycine, leucine, isoleucine and phenylalanine. The presence of an alanyl residue at this position drastically increases the inhibitory capacity of the compound, and therefore, this amino acid is particularly preferred. However, although activity is somewhat reduced, the remaining amino acids of this group may also occupy this position and still retain a significant level of inhibitory capacity.

The identity of additional amino acids, i.e. $AA_3$ if present, is not particularly critical to the activity of the inhibitors and therefore may be selected from any of the twenty amino acids, e.g., arginine, although the third amino acid is preferably glutamine, as this mimics the sequence adjacent to the cleavage site. As noted above, the length of the main acid sequence is not particularly critical, and the activity may be retained by the addition of up to as many as twenty or more amino acid residues. However, since the addition of several more residues does not significantly enhance the effectiveness of the compounds and substantially increases the difficulty of their preparation, it is preferred that the additional residues be limited to a maximum of two. Any of the amino acids used in the present peptides may be either the D or the L form; although the use of the D form may in some positions reduce activity somewhat, it may in some circumstances be desirable to sacrifice some activity for increase in stability of the product. It will also be understood that the term "amino acid" is intended to encompass both natural and synthetic residues; for example, it is contemplated that n-formyl tryptophan may be employed in any position where a tryptophan residue is called for or that halogenated forms may also be used in place of the naturally occurring form.

The compounds of the present invention are relatively simple to prepare. Preparation of the appropriate thiol acid starting materials, which are generally acetyl-protected, is achieved by art recognized procedures; a thorough discussion of the method of preparation is found in U.S. Pat. No. 4,235,885, the teachings of which are incorporated herein by reference. The peptides may be prepared by any of the wide range of known methods. Among the more commonly used techniques are coupling via the dicyclohexylcarbodiimide method, or the solid phase Merrifield synthesis, in which a protected amino acid is bound to a resin particle as an ester bond. Amino acids having functional groups such as tyrosine are generally protected with an easily removed blocking group, which are well known to the skilled artisan. Each of these techniques is equally suitable for the present purposes. The protected peptide is then coupled to the appropriate acetyl protected thiol, again by any of the typical coupling procedures referred to above. The compounds so produced may be purified by chromatography, electrophoresis, or any other suitable means, and the acetyl protecting group removed by treatment with dilute $NH_4OH$ in nitrogen-flushed methanol.

The present invention is also intended to encompass salts of the claimed peptides. These compounds form basic salts with various organic and inorganic bases. Among the salts which may be prepared are ammonium, alkali metal salts, alkaline earth metal salts and salts with organic bases such as dicyclohexamine. In those peptides in which Arg is added, acid addition salts may also be prepared, particularly acetate or hydrochloride salts. Although for obvious reasons, pharmaceutically acceptable salts are preferred, but the invention is not limited to them since non-pharmaceutically acceptable salts may prove useful in isolating the compounds of the invention.

The compounds of the invention contain an asymmetric carbon atom (C-2), and therefore exist as diastereomeric pairs, which can be resolved by chromatography. The invention therefore includes both the R and S isomers which may be used in isolation or as a racemic mixture.

The compounds disclosed herein have been demonstrated to be highly effective inhibitors of mammalian collagenase activity as shown in Table I. Many of the compounds are effective even in the nanomolar range, and all tested compounds have been proved effective in micromolar quantities. They may be thus efficiently employed in treatment of any mammalian disease in which collagenase has been implicated as a causative factor as noted above. Formulation of pharmaceutical compositions depends upon the nature of the condition to be treated. For example, for rheumatoid arthritis treatment, intraarticular injection may be the preferred mode of administration; the peptides in this case or for any other type of parenteral administration, will generally be administered with a pharmaceutically acceptable carrier such as a sterile solution containing other solutes, for example, sufficient saline or glucose to make the solution isotonic. The peptides may also be formulated into tablets or capsules for oral administration in combination with stabilizers, excipients, carriers, preservatives, or flavors, as is typical in pharmaceutical practice. The typical dosage is between 10–500 mg/kg of body weight of the mammal being treated.

The compounds of the present invention, their method of preparation and their use will be better understood by reference to the following non-limiting examples.

EXAMPLE 1

Preparation of $HSCH_2CH[CH_2CH(CH_3)_2]CO$-L-Phe-$NH_2$ 1. 2-(R,S)-[(Acetylthio)methyl]-4-methylpentanoyl-L-phenylalanine amide. To a stirring solution of (±) -2-acetylthiomethyl-4-methylpentanoic acid (800 mg, 3.92 mmol) in 10 ml dimethylformamide at 0° C. was added 0.43 ml N-methyl-morpholine (3.92 mmol) followed by a solution of dicyclohexylcarbodiimide in 4 ml dichloromethane. The solution was stirred overnight at room temperature. Solvents were removed in vacuo and the residue taken up in ethyl acetate and filtered. The filtrate was washed with solutions of 10% citric acid, 5% $NaHCO_3$, and 20% NaCl. After drying over $Na_2SO_4$, the solvent was removed by flash evaporation to give a solid which was triturated with pentane and filtered. The yield was 711 mg (52%). Two spots (presumably the expected diastereomers) were observed on TLC (silica gel 60) in two solvent systems [$R_f$ 0.38, 0.2 (50% ethyl acetate-hexane); $R_f$ 0.48, 0.35 (diethylether)].

Gas chromatographic-mass spectral analysis of the mixture showed a molecular ion of 350.1617 ($C_{18}H_{26}N_2O_3S$= 350.1664). The diastereomers were resolved by preparative $C_{18}$-reversed phase HPLC.

2. 2-[(R,S)-Mercaptomethyl]-4-methylpentanoyl-L-phenylalanine amide. The resolved diastereomers 1 and 2 were each dissolved in methanol, flushed with nitrogen for 15–30 minutes and treated with 0.1 volume of concentrated $NH_4OH$ for 30–60 minutes. The resulting deprotected thiol was precipitated by adding water, acidified with acetic acid, and the product recovered by lyophilization. For diastereomer 1:

Anal Calcd. for $C_{16}H_{24}N_2O_2S$ 0.2$H_2O$: C 61.58; H, 7.88; N, 8.98. Found: C, 61 46; H, 7 77; N, 9.08. For diastereomer 2: Anal. Calcd. for $C_{16}H_{24}N_2O_2S$ 0.1$H_2O$: C, 61.94; H, 7.86; N, 9.03. Found: C, 62.04; H, 7.91; N, 8.94.

EXAMPLE 2

Preparation of $HSCH_2CH[CH_2CH(CH_3)2]CO$-Phe-Ala-$NH_2$ 1. t-Butyloxycarbonyl-L-phenylalanyl-L-alanine amide. L-Alanine amide hydrobromide (500 mg, 2.95 mmol), t-butyloxcarbonyl-L-phenylalanine N-hydroxysuccinimide ester (885 mg, 2.95 mmol), and 0.41 ml (2.95 mmol) triethylamine were dissolved in 15 ml acetonitrile-methanol (2:1, v:v). The mixture was stirred overnight at room temperature. The solvent was then removed under reduced pressure at 40° C. and the residue extracted into ethyl acetate. The extract was washed successively with saturated $NaHCO_3$, water, 10% citric acid, and water. The organic layer was dried with $Na_2SO_4$ and the solvent removed by flash evaporation. The dried product weighed 0.6 g (61%).

2. L-Phenylalanyl-L-alanine amide trifluoroacetate. The product from step 1 above was dissolved in 3 ml trifluoroacetic acid. After 30 min at room temperature, the resulting deprotected peptide was precipitated with dry ether. The precipitate was collected by filtration, triturated with ether and dried. The yield was 0.58 g (111%).

3. 2-(R,S)-[(Acetylthio)methyl]-4-methylpentanoyl-L-phenylalanyl-L-alanine amide. L-Phenylalanyl-L-alanine amide trifluoroacetate (500 mg, 1.43 mmol), 0.2 ml triethylamine (1.43 mmol), 293 mg (±)-2-[(acetylthio)methyl]-4-methyl-pentanoic acid, and 320 mg (1.43 mmol) dicyclohexylcarbodiimide were dissolved in 10 ml of ice-cold acetonitrile-methanol (1:1, v:v). The reaction mixture was kept on ice overnight and its progress monitored at 210 nm by reversed phase HPLC using a $C_{18}$ column and a linear gradient of 0.1% $H_3PO_4$ and acetonitrile. In order to obtain complete reaction of the peptide, an additional 530 mg of the protected thiol and 375 mg of the carbodiimide were added over a 36 hour period. The reaction mixture was warmed to room temperature and the precipitate removed by filtration. The desired product peptide derivatives were purified by preparative $C_{18}$ reversed phase HPLC (0.1% trifluoroacetic acid/acetonitrile) and recovered by lyophilization (218 mg, 36%). The resulting mixture of diastereomers was separated into two components, designated diastereomer 1 and diastereomer 2, by reversed phase HPLC as above. Gas chromatographic-mass spectral analysis of 1 and 2 gave the same fragmentation pattern and showed molecular ions of 421.2043 and 421, respectively ($C_{21}H_{31}N_3O_4S$=421.2035).

4. 2-[(R,S)-Mercaptomethyl]-4-methylpentanoyl-L-phenylalanyl-L-alanine amide. The resolved diastereomers 1 and 2 were dissolved in 2 ml methanol, flushed with nitrogen for 15–30 minutes and treated with 0.2 ml concentrated $NH_4OH$ for 30–60 minutes. The resulting deprotected thiol was precipitated by adding water, acidified with acetic acid, and the product recovered by lyophilization. For diastereomer 1 (24 mg): TLC $R_f$ 0.31 ($CHCl_3$-MeOH, 10:1), 0.72 ($CHCl_3$-MeOH, 5:1), 0.92 (BuOH-acetic acid-$H_2O$, 4:1:1); amino acid analysis: Phe:Ala, 1:1.04; Anal. Calcd. for $C_{19}H_{29}N_3O_3S$ 1.4

$H_2O$: C, 56.38; H, 7.92; N, 10.38; S, 7.92. Found: C, 56.63; H, 7.55; N, 9.52; S, 8.18. For diastereomer 2 (80 mg): TLC $R_f$ 0.20 ($CHCl_3$-MeOH, 10:1), 0.67 ($CHCl_3$-MeOH, 5:1), 0.89 (BuOH-acetic acid-$H_2O$, 4:1:1); amino acid analysis; Phe:Ala, 1:0.86; Anal. Calcd for $C_{19}H_{29}N_3O_3S$ 1.9 $H_2O$; C, 55.15; H, 7 99; N, 10.16; S, 7.75. Found C, 55.40; H, 7.45; N 9.95; S, 7.96.

EXAMPLE 3

Preparation of $HSCH_2CH[CH_2CH(CH_3)_2]CO$-L-Phe-L-Leu-$NH_2$ 1. t-Butyloxycarbonyl-L-phenylalanyl-L-leucine amide. L-Leucine amide hydrochloride (500 mg, 2.99 mmol), t-butyloxycarbonyl-L-phenylalanine N-hydroxysuccinimide ester (1069 mg, 2.95 mmol), and 0.41 ml (2.95 mmol) triethylamine were dissolved in 10 ml acetonitrile-methanol (1:1, v:v). The mixture was stirred at room temperature overnight. The solvent was removed under reduced pressure at 40° C. and the residue extracted into ethyl acetate. The extract was washed successively with saturated $NaHCO_3$, water, 10% citric acid, and water. The organic layer was dried with $Na_2SO_4$ and the solvent removed by rotary evaporation as above. The dried product weighed 0.94 g (83.9%).

2. L-Phenylalanyl-L-leucine amide trifluoroacetate. The product from step 1 above was dissolved in 3 ml trifluoroacetic acid. After 30 min at room temperature, the product was precipitated with dry ether. The precipitate was collected by filtration, triturated with ether and dried. The yield was 0.94 g (108%).

3. 2-(R,S)-[(Acetylthio)methyl]-4-methylpentanoyl-L-phenylalanyl-L-leucine amide. L-Phenylalanyl-L-leucine amide trifluoroacetate (780 mg, 2.0 mmol), 0.28 ml triethylamine (2.0 mmol), 409 mg (±)-2-[(acetylthio)methyl]-4-methylpentanoic acid, and 513 mg (2.0 mmol), dicyclohexylcarbodiimide were dissolved in 10 ml ice-cold acetonitrile-methanol (1:1, v:v). The reaction mixture was kept on ice overnight and its progress monitored at 210 nm by reversed phase HPLC using a $C_{18}$ column and a linear gradient of 0.1% $H_3PO_4$ and acetonitrile. In order to obtain complete reaction of the peptide, and additional 530 mg of the protected thiol and 375 mg of the carbodiimide were added over a 36 hour period. The reaction mixture was warmed to room temperature and the precipitate removed by filtration. The product peptide derivatives were purified by preparative $C_{18}$ reversed phase HPLC (0.1% trifluoroacetic acid/acetonitrile) and recovered by lyophylization (440 mg, 47.5%). The resulting mixture of diastereomers were separated into two components, designated diastereomers 1 and diastereomer 2, by reversed phase HPLC as described above.

4. 2-[(R,S)-Mercaptomethyl]-4-methylpentanoyl-L-phenylalanyl-L-leucine amide. Each of the diastereomers were dissolved in 5 ml methanol, flushed with nitrogen for 15–30 minutes and treated with 0.5 ml concentrated $NH_4OH$ for 30–60 minutes. The resulting deprotected thiol was precipitated by adding water, acidified with acetic acid, and the product recovered by lyophilization. For diastereomer 1 (175 mg): TLC $R_f$ 0.19 ($CHCl_3$-MeOH, 10:1), 0.69 ($CHCl_3$-MeOH, 5:1), 0.97 (BuOH-acetic acid-$H_2O$ 4:1:1); amino acid analysis; Phe:Leu, 1:0.98; Anal. Calcd. for $C_{22}H_{35}N_3O_3S$ 1.2 $H_2O$: C, 59.62; H, 8.51; N, 9.48; S, 7.23. Found: C, 59.66; H, 8.51; N, 9.89; S, 6.61. For diastereomer 2 (160 mg): TLC $R_f$ 0.16 ($CHCl_3$-MeOH, 10:1), 0.67 ($CHCl_3$-MeOH, 5:1), 0.97 (BuOH-acetic acid-$H_2O$, 4:1:1); amino acid analysis: Phe:Leu, 1:1.01; Anal Calcd for $C_{22}H_{35}N_3O_3S$ 0.1 $H_2O$: C, 62.41; H, 8.38; N, 9.92; S, 7.57. Found: C, 62.11; H, 8.19; N, 9.59; S, 7.94.

EXAMPLE 4

The following example demonstrates the method of testing for inhibitory activity.

Collagenase Assay

Collagenase activity was determined after electrophoretic separation of degraded from undegraded type I collagen by polyacrylamide gel electrophoresis and densitometry as follows.

Acid-soluble calf skin collagen (0.25 mg/ml, approximately 0.8M) was incubated at 35° C. for 1 hr with pig synovial collagenase (0.04 μg protein) in 0.05M tris-HCL, 0.2M NaCl, 0.25M glucose, 5 mM $CaCl_2$, 10% dimethyl sulfoxide, pH 7.6 in a total reaction volume of 20 μL. Inhibitors were dissolved in dimethyl sulfoxide and the sulfhydryl titer determined in stock solutions immediately prior to use by the colorimetric procedure of Ellman [Ellman, G. L., Arch. Biochem. Biophys. 82: 70–77 (1959)]. At the end of the reaction period, the reactions were stopped by placing on ice and 20 μL sample dilution buffer was added [Laemmli, U. K., Nature (London) 227: 680–685 (1970)]. The samples were then placed in a boiling water bath for 2–5 minutes after which collagen degradation products were separated from undegraded collagen by sodium dodecyl sulfate-polyacrylamide electrophoresis according to the procedure of Laemmli [1970]. The electrophoretograms were fixed in isopropanol/acetic acid/water (100:40:300) and stained with 1% Coomassie Blue R-250. The percentage of collagen alpha chains degraded was estimated by scanning densitometry and integration of peak areas [Welgus et al., J. Biol. Chem. 256: 9511–9515 (1981)].

A spectrophotometric method was also utilized in some cases to determine collagenase activity [Lindy, S. et al., European J. Biochem. 156: 1–4 (1986)]. The conditions were the same as given above except that the reaction volume was 200 μL, the temperature was 37° C. and the enzyme concentration was 1.2 μg protein/ml. Stock solutions of inhibitors were prepared in 1 mM acetic acid in ethanol and the sulfhydryl titer determined colorimetrically by the method of Ellman (1956). The reaction progress was monitored for 6–10 minutes by following the increase in absorbance at 227 nm that accompanies denaturation of the collagen fragments. Initial rates of collagen degradation were determined from the linear portion of the progress curves.

The results of the collagenase assays for a number of the present peptides are found in Table I.

TABLE 1

| | | $IC_{50}$ (uM)* | |
|---|---|---|---|
| | | Fast Isomer | Slow Isomer |
| 1. | $HSCH_2CH[CH_2CH(CH_3)_2]CO$—Phe—$NH_2$ (with Cl substituent) | | 1 |
| 2. | $HSCH_2CH[CH_2CH(CH_3)_2]CO$—Trp—$NH_2$ | 1 | 2 |
| 3. | $HSCH_2CH[CH_2CH(CH_3)_2]CO$—Phe—Ala—$NH_2$ | 0.3 | 0.04 |
| 4. | $HSCH_2CH[CH_2CH(CH_3)_2]CO$—Trp—Ala—$NH_2$ | | 0.05 |
| 5. | $HSCH_2CH[CH_2CH(CH_3)_2]CO$—Phe—Leu—$NH_2$ | 10 | 4 |
| 6. | $HSCH_2CH[CH_2CH(CH_3)_2]CO$—Phe—Phe—$NH_2$ | | 2 |
| 7. | $HSCH_2CH[CH_2CH(CH_3)_2]CO$—Nal—Ala—$NH_2$ | | 0.03 |
| 8. | $HSCH_2CH[CH_2CH(CH_3)_2]CO$—Lys(t-Boc)—Ala—OEt | | 4 |

*IC refers to the approximate concentration of compound giving 50% inhibition of collagen degradation in an in vitro assay system using pig synovial collagenase. Because C-2 (containing the isobutyl side chain) is asymmetric, the compounds exist as diastereomeric pairs which can be resolved by chromatography. Where an individual diastereomer has been assayed, the result for each is reported. In cases where the diastereomers have not been resolved, the $IC_{50}$ values were obtained with a mixture containing approximately equal amounts of the two. Since the absolute configuration at C-2 is not known, the diastereomers are identified as 'fast' or 'slow' by their relative elution time from a $C_{18}$ reversed phase chromatographic system under standardized conditions.

EXAMPLE 5

Use of $HSCH_2CH[CH_2CH(CH_3)_2]CO$-Phe-Ala-$NH_2$ in the Treatment of Corneal Ulceration Caused by Alkali Burned Corneas

Qualitative Analysis

Collagenase, purified from sodium hydroxide burned rabbit corneal tissue, was placed in a reaction mixture containing Type I collagen (0.4 mg/ml), 0.005M Tris-HCl, 0.2M NaCl, 0.25M glucose, pH 7.7. Reactions were initiated by adding the enzyme to the reaction mixture; inhibitory potency was estimated by running separate reaction mixtures in which the peptide $HSCH_2CH[CH_2CH(CH_3)_2]$—CO-Phe-Ala-$NH_2$, made in accordance with Example 2, was added in varying concentrations to the mixture and incubated for 3 hours at 30° C. Other compounds were assayed for inhibitory potency in a similar manner. Reaction mixtures were quenched by placing them on ice and then adding one volume of sample dilution buffer followed by boiling the mixtures in a water bath for 5 minutes. Collagen degradation products were resolved from undegraded collagen by sodium dodecylsulfate-polyacylamide gel electrophoresis (SDS-PAGE) followed by staining with Coomassie Blue R-250. The SDS-PAGE assay was used to qualitatively evaluate the inhibitory capacity of the compounds tested. An estimate of inhibitory potency was then noted by visualizing the concentration range which produced 50% inhibition of collagen degradation.

The results of this qualitative assay are expressed as an $IC_{50}$ range (Table II). For example, doxycyline's $IC_{50}$ is 0.2 to 1.0 mM. That is, a doxycycline concentration of 0.2 to 1.0 mM is required to obtain a 50% inhibition of collagen degradation. These estimated ranges were then used to predict the inhibitor concentrations tested in the quantitative analysis detailed below.

Quantitative Analysis

Quantitative determination of collagenase activity was carried out with a fluorogenic peptide substrate, Dnp-Pro-Leu-Gly-Leu-Trp-Ala-D-Arg-$NH_2$, which collagenase cleaves to produce Dnp-Pro-Leu-Gly and Leu-Trp-Ala-D-Arg-$NH_2$. The rate of production of the tetrapeptide was monitored with an AMINCO-BOWMAN® spectrofluorometer (excitation wavelength of 280 nm and emission wavelength of 346 nm). This test was repeated using high performance liquid chromatography (HPLC) to separate and detect the two cleaved collagenase products.

Reaction mixtures for both the fluorometric and HPLC assays contained 0.05M Tris-HCl, 0.2M NaCl, 10 mM $CaCl_2$, and Dnp-substrate 20 uM, pH 7.7. The peptide of Example 2 was added to the assay mixtures at varying concentrations. The incubation conditions differed between the two assays; the fluorometric reaction mixtures were incubated at 37° C. for 2 to 3 minutes whereas the HPLC reaction mixtures were incubated at 37° C. for 3 hours. This was necessary because the HPLC assay was not as sensitive in detecting the substrate cleavage products as the fluorometric assay. $IC_{50}$ values were interpolated from plots of $log[A_o/A_i)-1[$ vs. $log[Inhibitor]$, where $A_o$ is the activity observed in the absence of inhibitor and $A_i$ is the activity observed in the presence of inhibitor at concentration i.

The results of these tests are summarized in Tables II to IV. Table II tabulates the estimated $IC_{50}$ value for the peptide made in accordance with Example 2, denotes as "Synthetic Peptide." Table III provides the same value by the quantitative fluorometric assay. Table IV yields the same result determined by HPLC assay.

COMPARATIVE EXAMPLE 1

Example 5 was repeated except that the inhibitor of that example was replaced with other known and currently used corneal ulceration inhibitors. The inhibitors tested were sodium citrate, cysteine, doxycycline, minocycline, tetracycline, acetylcysteine and ascorbic acid. The results of these tests appear in Tables II to IV.

TABLE II

| INHIBITOR POTENCIES BY SDS-PAGE | |
|---|---|
| Inhibitor | Estimated $IC_{50}$ Range (mM) |
| Synthetic Peptide | 0.001–0.003 |
| Sodium Citrate* | 10–30 |
| Cysteine | 3–10 |
| Acetylcysteine | 10–30 |
| Tetracycline | 1–2 |
| Doxycycline | 0.2–1 |
| Sodium Ascorbate | No Inhibition |

*Reversed by addition of excess Ca++

TABLE III

| Inhibitor Potencies by Fluorometric Assay | |
|---|---|
| Inhibitor | $IC_{50}$ |
| Synthetic Peptide | $1.1 \times 10^{-5}$ mM |
| Sodium Citrate | 45 mM |

TABLE IV

| Inhibitor Potencies by HPLC Assay | |
|---|---|
| Inhibitor | $IC_{50}$ |
| Synthetic Peptide | $1.0 \times 10^{-4}$ mM |
| Doxycycline | $1.5 \times 10^{-2}$ mM |
| Minocycline | 0.19 mM |
| Tetracycline | 0.35 mM |
| Cysteine | 0.37 mM |
| Acetylcysteine | 2.7 mM |
| Ascorbic Acid | No Inhibition |

EXAMPLE 6 AND COMPARATIVE EXAMPLE 2

Use of $HSCH_2CH[CH_2CH(CH_3)_2]CO$-Phe-Ala-$NH_2$ in the Treatment of Corneal Ulceration by Alkali-Burned Corneas Following the in vitro studies which documented the high potency of the peptide, the peptide was tested in an in vivo model of alkali-burned rabbit corneas. Following a standard alkali burn (2N NaOH×60 seconds) to one eye, 9 rabbits were treated with a 1 mM solution of $HSCH_2CH[CH_2CH(CH_3)_2]CO$-Phe-Ala-$NH_2$ both topically (6 times per day) and by subconjunctival injection (once daily) for three weeks. Ten control rabbits received topical and subconjunctival administration of vehicle only. Corneal ulceration occurred in 100% of the control animals and perforation occurred in 70%. Experimental eyes had an incidence of 44% ulceration and no perforation (P<0.01). These findings, summarized in Table V, demonstrate that the peptide is capable of preventing alkali-induced corneal ulceration and perforation in rabbits.

TABLE V

| Analysis of Degree of Corneal Ulceration and Perforation Occurring After Experimental Alkali Burns | | | | |
|---|---|---|---|---|
| Ex. No. | Treatment Group | % Overall Ulceration | % Deep Ulcers | % Perforation |
| CE2 | Control (n = 10) | 100% | 80% | 70% |
| 6 | $HSCH_2CH[CH_2CH(CH_3)_2]$-CO—Phe—Ala—$NH_2$ | 44% | 11% | 0% |

EXAMPLE 7

Use of $HSCH_2CH[CH_2CH(CH_3)_2]CO$-Phe-Ala-$NH_2$ in a Treatment of Corneal Ulceration Caused by Pseudomonas Aeruginosa Pseudomonas aeruginosa proteases were obtained by overnight incubation of virulent strain of Pseudomonas aeruginosa (PA) on tryptone glucose extract agar. A single enzyme, presumably PA elastase, was purified and separated by an affinity matrix. The enzyme had a $K_m$ of 20 um for DNP-Pro-Leu-Gly-Leu-Trp-Ala-D-Arg-$NH_2$.

The PA elastase was tested in accordance with the procedures analogous to those conducted on purified collagenase in Example 5. The results of this test established that 50% inhibition, $IC_{50}$, requires a peptide concentration of $3 \times 10^{-4}$ mM.

COMPARATIVE EXAMPLE 3

Use of Inhibitors of the Prior Art in a Treatment of Corneal Ulceration Caused by Pseudomonas aeruginosa Example 7 was repeated using three corneal ulceration treatments of the prior art: Tetracycline, minocycline and doxycycline. The results of Examples 7 and Comparative Example 3 are summarized in Table VI below.

TABLE VI

| Example No. | Inhibitor | $IC_{50}$ |
|---|---|---|
| 7 | Synthetic Peptide | $3.0 \times 10^{-4}$ mM |
| CE3 | Tetracycline | 0.66 mM |
| CE3 | Minocycline | 0.26 mM |
| CE3 | Doxycycline | 0.11 mM |

The above embodiments and examples are given to illustrate the scope and spirit of the instant invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A pharmaceutical composition comprising a pharmaceutically effective amount of a compound having the formula:

$$R_1\ S\ CH\ (R_2)\ CH\ (R_3)\ CO\text{-}AA_1\text{-}(AA_2)_m\text{---}X$$

or pharmaceutically acceptable salts thereof
wherein
  m is an integer 0 or 1;
  $AA_1$ is phenylalanine, naphthylalanine, tryptophan, tyrosine or ε-amino blocked lysine;
  $AA_2$ is alanine, glycine, phenylalanine or isoleucine;
  $R_1$ is hydrogen, alkyl having 1–10 carbon atoms, alkanoyl having 2–10 carbon atoms, or aroyl having from 7–11 carbon atoms;
  $R_2$ is hydrogen or alkyl having from 1–6 carbon atoms;
  $R_3$ is alkyl having from 2–10 carbon atoms, cycloalkyl having from 3–6 carbon atoms; aryl or arylalkyl wherein the aryl moieties have from 6–10 ring carbon atoms;
  X is $NH_2$, [OH,] $OCH_3$ or $OCH_2CH_3$, and a pharmaceutical carrier therefor.

2. The pharmaceutical composition according to claim 1 wherein $R_3$ is an alkyl.

3. The pharmaceutical composition according to claim 2 wherein $R_3$ is a branched alkyl.

4. The pharmaceutical composition according to claim 1 wherein $R_3$ is alkyl having 4 carbon atoms.

5. The pharmaceutical composition according to claim 1 wherein $R_3$ is isobutyl.

6. The pharmaceutical composition according to claim 1 wherein $R_3$ is isobutyl and $R_2$ is hydrogen.

7. The pharmaceutical composition according to claim 1 wherein $R_2$ is hydrogen or $CH_3$, $R_3$ is isobutyl, $R_1$ is hydrogen and X is $NH_2$ or $OCH_2CH_3$.

8. The pharmaceutical composition of claim 1 wherein m is 1 and $AA_2$ is alanine.

9. The pharmaceutical composition according to claim 1 wherein $R_2$ is hydrogen or $CH_3$, $R_3$ is isobutyl, $R_1$ is hydrogen and X is $NH_2$ or $OCH_2CH_3$, m is 1 and $AA_2$ is alanine.

10. The pharmaceutical composition according to claim 1 wherein the compound has the formula:

HS $CH_2$ CH [$CH_2CH(CH_3)_2$] CO—Nal—$NH_2$;
HS $CH_2$ CH [$CH_2CH(CH_3)_2$] CO—Phe—$NH_2$;
HS $CH_2$ CH [$CH_2CH(CH_3)_2$] CO—Trp—$NH_2$;
HS $CH_2$ CH [$CH_2CH(CH_3)_2$] CO—Phe—Ala—$NH_2$;
HS $CH_2$ CH [$CH_2CH(CH_3)_2$] CO—Trp—Ala—$NH_2$;
HS $CH_2$ CH [$CH_2CH(CH_3)_2$] CO—Nal—Ala—$NH_2$;
HS $CH_2$ CH [$CH_2CH(CH_3)_2$] CO—Phe—Phe—$NH_2$; or
HSCH$_2$CH[CH$_2$CH(CH$_3$)$_2$]CO—Lys—Ala—OCH$_2$—CH$_3$.
                                          |
                                       (t-Boc)

11. The pharmaceutical composition according to claim 1 wherein the compound has the formula:

HS $CH_2$ CH[$CH_2$(CH(CH$_3$)$_2$)] CO-Phe-Ala-$NH_2$.

12. A pharmaceutical composition comprising a pharmaceutically effective amount of a compound having the formula:

$$R_1\ S\ CH\ (R_2)\ CH\ (R_3)\ CO\text{-}AA_1\text{-}(AA_2)_m\text{---}X$$

wherein
  m is 0 or 1;
  $AA_1$ is phenylalanine, naphthylalanine, tryptophan, tyrosine or ε-amino blocked lysine;
  $AA_2$ is leucine;
  $R_1$ is hydrogen, alkyl having 1–10 carbon atoms, alkanoyl having from 2–10 carbon atoms or aroyl having from 7–11 carbon atoms;
  $R_2$ is hydrogen or alkyl having from 1–6 carbon atoms;
  $R_3$ is alkyl having 2–10 carbon atoms, cycloalkyl having from 3–6 carbon atoms, aryl or arylalkyl, wherein the aryl moieties have from 6–10 carbon atoms; and
  X is $NH_2$, [OH,] $OCH_3$ or $OCH_2CH_3$ and a pharmaceutical carrier therefor.

13. The pharmaceutical composition according to claim 12 wherein $R_3$ is alkyl.

14. The pharmaceutical composition according to claim 13 wherein $R_3$ is a branched alkyl having 4 carbon atoms.

15. The pharmaceutical composition according to claim 12 wherein $R_3$ is isobutyl.

16. The pharmaceutical composition according to claim 12 wherein $R_3$ is isobutyl and $R_2$ is hydrogen.

17. The pharmaceutical composition according to claim 12 wherein $R_2$ is hydrogen or $CH_3$, R.is isobutyl, $R_1$ is hydrogen and X is $NH_2$ or $OCH_2CH_3$.

18. The pharmaceutical composition according to claim 12 wherein the compound has the formula:

HS $CH_2$ CH[$CH_2CH(CH_3)_2$] CO Phe-Leu-$NH_2$.

19. A method of reducing the adverse effects of mammalian collagenase in a mammal which comprises administering to said mammal a pharmaceutically effective amount of a compound of the formula:

$$R_1\ S\ CH\ (R_2)\ CH\ (R_3)\ CO\text{-}AA_1\text{-}\ (AA_2)m\text{---}X$$

or pharmaceutically acceptable salts thereof wherein m is an integer 0 or 1;

AA$_1$ is phenylalanine, naphthylalanine, tryptophan, tyrosine or ε-amino blocked lysine;

AA$_2$ is alanine, glycine, phenylalanine or isoleucine;

R$_1$ is hydrogen, alkyl having 1–10 carbon atoms, alkanoyl having 2–10 carbon atoms, or aroyl having from 7–11 carbon atoms;

R$_2$ is hydrogen or alkyl having from 1–6 carbon atoms;

R$_3$ is alkyl having from 2–10 carbon atoms, cycloalkyl having from 3–6 carbon atoms, aryl or arylalkyl wherein the aryl moieties have from 6–10 ring carbon atoms;

X is NH$_2$, OH, OCH$_3$ or OCH$_2$CH$_3$.

20. The method according to claim 19 wherein R$_3$ is alkyl.

21. The method according to claim 20 wherein R$_3$ is a branched alkyl.

22. The method according to claim 21 wherein R$_3$ is alkyl having 4 carbon atoms.

23. The method according to claim 22 wherein R$_3$ is isobutyl.

24. The method according to claim 19 wherein R$_3$ is isobutyl and R$_2$ is hydrogen.

25. The method according to claim 19 wherein R$_2$ is hydrogen or CH$_3$, R$_3$ is isobutyl, R$_1$ is hydrogen and X is NH$_2$ or OCH$_2$CH$_3$.

26. The method according to claim 19 wherein m is 1 and AA$_2$ is alanine.

27. The method according to claim 19 wherein R$_2$ is hydrogen or CH$_3$, R$_3$ is isobutyl, R$_1$ is hydrogen and X is NH$_2$ or OCH$_2$CH$_3$, m is 1 and AA$_2$ is alanine.

28. The method according to claim 19 wherein the compound has the formula:

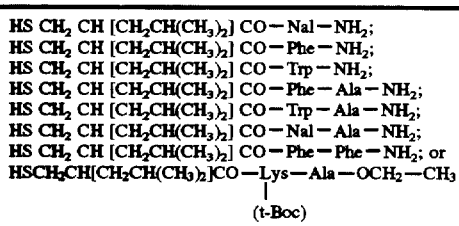

29. The method according to claim 19 wherein the compound has the formula:

HS CH$_2$ CH [CH$_2$CH(CH$_3$)$_2$] CO-Phe-Ala-NH$_2$.

30. The method of claim 19 wherein said disorder is rheumatoid arthritis.

31. The method of claim 19 wherein said disorder is periodontal disease.

32. The method of claim 19 wherein said disorder is tumor metastasis.

33. A method of reducing the adverse effects of mammalian collagenase in a mammal which comprises administering to said mammal a pharmaceutically effective amount of a compound of the formula:

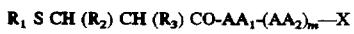

wherein m is an integer 0 or 1;

AA$_1$ is phenylalanine, naphthylalanine, tryptophan, tyrosine or ε-amino blocked lysine;

AA$_2$ is leucine;

R$_1$ is hydrogen, alkyl having 1–10 carbon atoms, alkanoyl having from 2–10 carbon atoms or aroyl having from 7–11 carbon atoms;

R$_2$ is hydrogen or alkyl having from 1–6 carbon atoms;

R$_3$ is alkyl having 2–10 carbon atoms, cycloalkyl having from 3–6 carbon atoms, aryl or arylalkyl, wherein aryl moieties have from 6–10 carbon atoms;

X is NH$_2$, OH, OCH$_3$ or OCH$_2$CH$_3$.

34. The method according to claim 33 in which R$_3$ is alkyl.

35. The method according to claim 33 wherein R$_3$ is a branched alkyl having 4 carbon atoms.

36. The method according to claim 33 wherein R$_3$ is isobutyl.

37. The method according to claim 33 wherein R$_3$ is isobutyl and R$_2$ is hydrogen.

38. The method according to claim 33 wherein R$_2$ is hydrogen or CH$_3$, R$_3$ is isobutyl, R$_1$ is hydrogen and X is NH$_2$ or OCH$_2$CH$_3$.

39. The method according to claim 33 wherein the compound is

HS CH$_2$ CH[CH$_2$CH(CH$_3$)$_2$] CO-Phe-Leu-NH$_2$.

40. The method of claim 33 wherein said disorder is rheumatoid arthritis.

41. The method of claim 33 wherein said disorder is periodontal disease.

42. The method of claim 33 wherein said disorder is tumor metastasis.

43. A method for treating corneal ulceration in mammals comprising administering to a mammal in need of such treatment a corneal ulceration inhibiting effective amount of a compound having the formula:

or pharmaceutically acceptable salts thereof wherein m is an integer 0 or 1;

AA$_1$ is phenylalanine, naphthylalanine, tryptophan, tyrosine or ε-amino blocked lysine;

AA$_2$ is alanine, glycine, phenylalanine or isoleucine;

R$_1$ is hydrogen, alkyl having 1–10 carbon atoms, alkanoyl having 2–10 carbon atoms, or aroyl having from 7–11 carbon atoms;

R$_2$ is hydrogen or alkyl having from 1–6 carbon atoms;

R$_3$ is alkyl having from 2–10 carbon atoms, cycloalkyl having from 3–6 carbon atoms; aryl or arylalkyl wherein the aryl moieties having from 6–10 ring carbon atoms;

X is NH$_2$, OH, OCH$_3$ or OCH$_2$CH$_3$.

44. The method of claim 43 wherein said corneal ulceration is the result of alkali burning of the cornea.

45. The method of claim 43 wherein said corneal ulceration is the result of infectious keratitis.

46. The method of claim 45 wherein said infectious keratosis is induced by infection by *Pseudomonas aeruginosa*.

47. A method for treating corneal ulceration in mammals comprising administering to a mammal having corneal ulceration a corneal ulceration inhibiting effective amount of a compound having the formula:

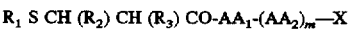

wherein m is an integer 0 or 1;

AA$_1$ is phenylalanine, naphthylalanine, tryptophan, tyrosine, or ε-amino blocked lysine;

AA$_2$ is leucine;

$R_1$ is hydrogen, alkyl having 1–10 carbon atoms, alkanoyl having from 2–10 carbon atoms or aroyl having from 7–11 carbon atoms;

$R_2$ is hydrogen or alkyl having from 1–6 carbon atoms;

$R_3$ is alkyl having 2–10 carbon atoms, cycloalkyl having from 3–6 carbon atoms, aryl or arylalkyl, wherein aryl moieties have from 6–10 carbon atoms;

X is $NH_2$, OH, $OCH_3$ or $OCH_2CH_3$.

48. The method of claim 47 wherein said corneal ulceration is the result of alkali burning of the cornea.

49. The method of claim 47 wherein said corneal ulceration is the result of infectious keratitis.

50. The method of claim 49 wherein said infectious keratosis is induced by infection by *Pseudomonas aeruginosa*.

51. The method according to claim 43 wherein $R_3$ is alkyl having 4 carbon atoms.

52. The method according to claim 43 wherein $R_3$ is branched alkyl.

53. The method according to claim 43 wherein $R_3$ is isobutyl.

54. The method according to claim 43 wherein $R_3$ is isobutyl and $R_2$ is hydrogen.

55. The method according to claim 43 wherein $R_2$ is hydrogen or $CH_3$, $R_3$ is isobutyl, $R_1$ is hydrogen and X is $NH_2$ or $OCH_2CH_3$.

56. The method according to claim 43 wherein m is 1 and $AA_2$ is alanine.

57. The method according to claim 43 wherein $R_2$ is hydrogen or $CH_3$, $R_3$ is isobutyl, $R_1$ is hydrogen and X is $NH_2$ or $OCH_2CH_3$, m is 1 and $AA_2$ is alanine.

58. The method according to claim 43 wherein the compound has the formula:

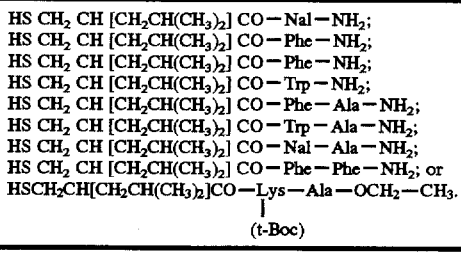

59. The method according to claim 43 wherein the compound is

60. The method according to claim 47 wherein $R_3$ is a branched alkyl having 4 carbon atoms.

61. The method according to claim 47 wherein $R_3$ is isobutyl.

62. The method according to claim 47 wherein $R_3$ is isobutyl and $R_2$ is hydrogen.

63. The method according to claim 47 wherein $R_2$ is hydrogen or $CH_3$, $R_3$ is isobutyl, $R_1$ is hydrogen and X is $NH_2$ or $OCH_2CH_3$.

64. The method according to claim 47 wherein the compound has the formula:

65. A compound of the formula:

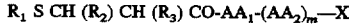

or pharmaceutically acceptable salts thereof wherein m is an integer 0 or 1;

$AA_1$ is phenylalanine, naphthylalanine, tryptophan, tyrosine or ε-amino blocked lysine $AA_2$ is alanine, glycine, Phenylalanine or isoleucine, $R_1$ is hydrogen, alkyl having 1–10 carbon atoms, alkanoyl having 2–10 carbon atoms, or aroyl having from 7–11 carbon atoms, $R_2$ is hydrogen or alkyl having 1–6 carbon atoms, $R_3$ is alkyl having from 2–10 carbon atoms, cycloalkyl having from 3–6 carbon atoms, aryl or arylalkyl wherein the aryl moieties have from 6–10 ring carbon atoms; and X is $NH_2$, [OH,] $OCH_3$ or $OCH_2CH_3$.

66. The compound according to claim 65 wherein $R_3$ is alkyl.

67. The compound according to claim 65 wherein $R_3$ is a branched alkyl.

68. The compound according to claim 65 wherein $R_3$ is alkyl having 4 carbon atoms.

69. The compound according to claim 65 wherein $R_3$ is isobutyl.

70. The compound according to claim 65 wherein $R_3$ is isobutyl and $R_2$ is hydrogen.

71. The compound according to claim 65 wherein $R_2$ is hydrogen or $CH_3$, $R_3$ is isobutyl, $R_1$ is hydrogen and X is $NH_2$ or $OCH_2CH_5$.

72. The compound according to claim 65 wherein m is 1 and $AA_2$ is alanine.

73. The compound according to claim 65 wherein $R_2$ is hydrogen or $CH_3$, $R_3$ is isobutyl, $R_1$ is hydrogen and X is $NH_2$ or $OCH_2CH_3$, m is 1 and $AA_2$ is alanine.

74. The compound according to claim 65 wherein the compound has the formula:

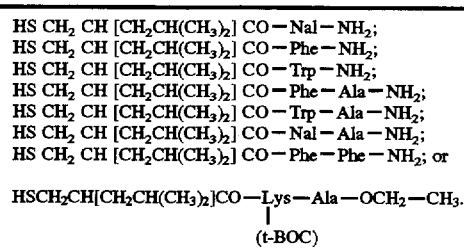

75. The compound according to claim 65 wherein the compound is

76. A compound having the formula:

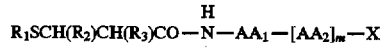

wherein m is an integer 0 or 1;

$AA_1$ is phenylalanine, naphthylalanine, tryptophan tyrosine or ε-amino blocked lysine;

$AA_2$ is leucine;

$R_1$ is hydrogen, alkyl having 1–10 carbon atoms, alkanoyl having from 2–10 carbon atoms or aroyl having from 7–11 carbon atoms;

$R_2$ is hydrogen or alkyl having from 1–6 carbon atoms;

$R_3$ is alkyl having 2–10 carbon atoms, cycloalkyl having from 3–6 carbon atoms, aryl or arylalkyl, wherein aryl moieties have from 6–10 carbon atoms;

X is $NH_2$, $OCH_3$ or $OCH_2CH_3$.

77. The compound according to claim 76 in which $R_3$ is alkyl.

78. The compound according to claim 76 wherein $R_3$ is a branched alkyl having 4 carbon atoms.

79. The compound according to claim 76 wherein $R_3$ is isobutyl.

80. The compound according to claim 76 wherein $R_3$ is isobutyl and $R_2$ is hydrogen.

81. The compound according to claim 76 wherein $R_2$ is hydrogen or $CH_3$, $R_3$ is isobutyl, $R_1$ is hydrogen and X is $NH_2$ or $OCH_2CH_3$.

82. The compound according to claim 76 having the formula:

$$HS\ CH_2\ CH[CH_2CH(CH_3)_2]\ CO\text{-Phe-Leu-}NH_2.$$

83. A compound of the formula:

$$R_1\ SCH\ (R_2)CH(R_3)\ CO\text{-}AA_1(AA_2)_m(AA_3)_n\text{---}X$$

wherein $AA_1$ is phenylalanine, naphthylalanine, tryptophan tyrosine or ε-amino blocked lysine;

$AA_2$ is alanine, glycine, phenylalanine, leucine or isoleucine, $AA_3$ is glutamine or arginine, m is an integer 0 or 1, n is an integer 1 or 2, $R_1$ is hydrogen, alkyl having 1–10 carbon atoms, alkanoyl having 2–10 carbon atoms, or aroyl having from 7–11 carbon atoms, $R_2$ is hydrogen or alkyl having 1–6 carbon atoms, $R_3$ is alkyl having from 2–10 carbon atoms, cycloalkyl having from 3–6 carbon atoms, aryl or arylalkyl wherein the aryl moieties have from 6–10 ring carbon atoms, and X is $NH_2$, OH, $OCH_3$ or $OCH_2CH_3$.

84. The compound according to claim 83 wherein $R_3$ is alkyl.

85. The compound according to claim 83 wherein $R_3$ is branched alkyl.

86. The compound according to claim 83 wherein $R_3$ is alkyl having 4 carbon atoms.

87. The compound according to claim 83 wherein $R_3$ is isobutyl.

88. The compound according to claim 83 wherein $R_3$ is isobutyl and $R_2$ is hydrogen.

89. The compound according to claim 83 wherein $R_2$ is hydrogen or $CH_3$, $R_3$ is isobutyl, $R_1$ is hydrogen and X is $NH_2$ or $OCH_2CH_2$.

90. The compound according to claim 83 wherein m is 1 and $AA_2$ is alanine.

91. The compound according to claim 83 wherein $R_2$ is hydrogen or $CH_3$, $R_3$ is isobutyl, $R_1$ is hydrogen and X is $NH_2$ or $OCH_3$ $OCH_2CH_3$, m is 1 and $AA_2$ is alanine.

92. The compound of claim 83 wherein n is 1 and $AA_3$ is glutamine or arginine.

93. The compound of claim 83 wherein the compound has the formula:

$$HS\ CH_2\ CH[CH_2\ CH(CH_3)_2]\ CO\text{-Phe-Ala-Arg-}NH_2.$$

94. A pharmaceutical composition comprising a pharmaceutically effective amount of a compound according to claim 83 and a pharmaceutical carrier therefor.

95. A method of inhibiting the degradation of collagen in mammals by mammalian collagenase comprising administering to said mammal an inhibiting effective amount of a compound according to claim 83.

96. A method for treating corneal ulceration in mammals comprising administering to said mammal a corneal ulceration inhibiting effective amount of a compound according to claim 83.

* * * * *